US00PP26870P2

(12) United States Plant Patent
Kordes

(10) Patent No.: US PP26,870 P2
(45) Date of Patent: Jun. 28, 2016

(54) GRANDIFLORA ROSE PLANT NAMED 'KORBAMFLU'

(50) Latin Name: *Rosa hybrida*
Varietal Denomination: KORbamflu

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Sohne Rosenschulen GmbH & Co. KG, Offenseth-Sparrieshoop (DE)

( * ) Notice: Subject to any disclaimer, the term of this patent is extended or adjusted under 35 U.S.C. 154(b) by 98 days.

(21) Appl. No.: 14/120,937

(22) Filed: Jul. 11, 2014

(51) Int. Cl.
*A01H 5/02* (2006.01)

(52) U.S. Cl.
USPC ..... Plt./135

(58) Field of Classification Search
USPC ..... Plt./135, 130, 105, 146, 141
See application file for complete search history.

(56) References Cited

PUBLICATIONS

Help me find Roses, Clematis and Peonies retrieved on Dec. 3, 2015, retrieved from the Internet at <https://www.helpmefind.com/rose/pl.php?n=95759> 1 page.*

* cited by examiner

*Primary Examiner* — June Hwu

(57) ABSTRACT

A new and distinct variety of rose with long lasting, novel orange-red flowers, and attractive foliage with very good disease resistance. It exhibits upright growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORbamflu'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2002. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORbamflu'.

SUMMARY OF THE INVENTION

The new rose plant may be distinguished from its seed parent, an un-named seedling, by the following combination of characteristics:

1. 'KORbamflu' has very good disease resistance, whereas the un-named seedling has average disease resistance.
2. 'KORbamflu' has orange blooms, whereas the un-named seedling has golden yellow blooms.

The new rose plant may be distinguished from its pollen parent, an un-named seedling, by the following combination of characteristics:

1. 'KORbamflu' has orange blooms, whereas the un-named seedling has golden yellow blooms.
2. 'KORbamflu' has large blooms, whereas the un-named seedling has very large blooms.

The objective of the hybridization was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORbamflu' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORbamflu' was selected in May 2003 from the seedling beds to be asexually propagated for further evaluation. The first asexual propagation of 'KORbamflu' was done by budding in July 2003 at the inventor's nursery in Offenseth-Sparrieshoop, Germany.

These initial and other subsequent propagations conducted in controlled environments demonstrate that 'KORbamflu' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORbamflu'.

DETAILED BOTANICAL DESCRIPTION

The following is a description of 'KORbamflu', as observed growing in June 2014 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORliolow', a rose variety from the same inventor described and illustrated in U.S. Plant Pat. No. 21,472 and issued on Nov. 16, 2010, are compared to 'KORbamflu' in Chart 1.

CHART 1

| Characteristic | 'KORbamflu' | 'KORliolow' |
|---|---|---|
| Petal count under normal conditions. | Approximately 125 to 135. | Approximately 60-65. |
| Number of leaflets on normal leaves in the middle of the stem. | Normally 7. | Normally 3 to 5. |
| Average flower diameter. | 75 to 90 mm. | 70 to 75 mm. |

Parents:

*Seed parent*.—An un-named seedling.

*Pollen parent*.—An un-named seedling.

Classification:

*Botanical classification*.—*Rosa hybrida* 'KORbamflu'.

*Commercial classification*.—Grandiflora rose.

FLOWER AND FLOWER BUD

Blooming habit: Recurrent.

Flower bud:

*Size*.—Upon opening, 45 mm in length from base of receptacle to distal end of bud and 45 mm diameter at its widest point.

*Bud form*.—Short. Globular.

*Bud color*.—As sepals first unfold, bud color is Red Group 50A. When ¼ open, the upper surface of petals is Red Group 38B, and the lower surface is Red Group 52D. Outermost petals are Red Group 52D with intonations of Red Group N66A.

*Sepals*.—Color: Upper surface: Yellow-Green Group 147C. Lower surface: Yellow-Green Group 144A. Size: Average 34 to 45 mm (l)×12 to 13 mm (w). Shape: Weak foliaceous appendages on two to three of the five sepals. Apex: Typically apiculate, occasionally cirrose. Base: Flat at union with receptacle. Quantity: Five. Surface texture: Upper side: Silky, strongly pubescent. Lower surface: Smooth, lightly pubescent. Margins: Cilliate. Stipitate glands: Limited.

Flower bloom:

*Fragrance*.—Light.

*Duration*.—On the plant 5 to 8 days. Senesced petals drop away cleanly.

*Size*.—Large for a grandiflora rose. When open, the average flower diameter is 75 to 90 mm and the average flower height is 30 to 35 mm.

*Form*.—Shape of flower when viewed from the side: Upon opening, upper part: Flat. Upon opening, lower part: Flat. Open flower, upper part: Flat. Open flower, lower part: Concave.

Color:

*Upon opening, petals*.—Outermost petals: Outer Side: Variable. Red Group 49A with intonations of Orange Group 25A, 25B and 25C. Inner Side: Variable. Red Group 38C with intonations of Orange Group 25B, 25C and 25D. Innermost petals: Outer Side: Red Group 41A. Inner Side: Orange Group N25A.

*Upon opening, basal petal spots*.—Basal petal spot size, inner side: Medium. Basal petal spot, outermost petals: Outer Side: Yellow Group 4A. Inner Side: Yellow Group 5A. Basal petal spot, innermost petals: Outer Side: Yellow Group 5A. Inner Side: Yellow Group 12A.

*After opening, petals*.—Outermost petals: Outer Side: Variable. Red Group 49C and 49D with intonations of Red-Purple Group N66B in the marginal zone, Orange Group 29B, 29C and 29D with intonations of Red-Purple Group N66B in the middle zone, Yellow Group 12C in the basal zone. Inner Side: Variable. Red Group 50D with intonations of Red Group 50A in the marginal zone. Orange Group 29B, 29C and 29D in the middle zone. Yellow Group 12B in the basal zone. Basal petal spot is medium sized. Innermost petals: Outer Side: Variable. Red Group 37C and 37D in the marginal zone. Orange Group 19A and 19B in the middle zone. Yellow Group 12B in the basal zone. Inner Side: Variable. Orange Group 24C and 24D with intonations for Red-Purple Group N66B in the marginal zone. Orange Group 24C and 24D in the middle zone. Yellow Group 12B in the basal zone. Basal petal spot is medium sized. After opening, no distinctive coloration at petal base observed.

General tonality: On open flower Orange-Red Group 32C. No change in the general tonality at the end of the 4th day. Afterwards, general tonality is Orange Group 29C to 29D.

Petals:

*Petal count*.—Very double.

*Average range*.—Approximately 125 to 135 petals under normal conditions.

*Petal reflex*.—Petals reflex somewhat.

*Petal margin*.—Typically entire, with outermost petal margins occasionally undulated or erose.

*Petal shape*.—Outermost petals: Orbicular. Apex: Obtuse. Base: Obtuse. Innermost petals: Obtuse. Apex: Obtuse. Base: Cuneate to attenuate.

*Petal size*.—20 to 40 mm (l)×15 to 45 mm (w).

*Petal arrangement*.—Not formal. Nearly quartered rosette.

*Texture*.—Smooth.

Petaloids:

*Petaloid count*.—Average of 55 per flower.

*Petaloid size*.—Variable: 6 to 25 mm (l)×2 to 20 mm (w).

*Petaloid color*.—Inner side: Orange-Red Group 32B and 32C with intonations of Yellow Group 5C along the midrib. Outer side: Red Group 4C to 4D, with intonations of Yellow Group 5 along the midrib.

*Petaloid texture*.—Smooth.

*Margins*.—Undulated.

*Petaloid shape*.—Most commonly spatulate. Apex: Acute. Base: Attenuate.

Reproductive organs:

*Pistils*.—Average. Approximately 70 present.

*Stigmas*.—Location: Variable. Innermost stigma inferior in position to anthers, transitioning to outermost stigma being superior in position to anthers. Color: Greyed-Yellow Group 162A.

*Styles*.—Length: 3 to 10 mm long. Color: Green-White Group 157A.

*Stamens*.—Approximately 50 on average and regularly arranged. Anthers: Size: Average 2.5 mm (l)×1 mm (w). Pollen: Generally present. Color: Greyed-Orange Group N163C and 164A. Filaments: Color: Yellow Group 13B and 13C. Length: 5 to 7 mm.

*Receptacle*.—Surface: Smooth. Color: Yellow-Green Group 144A. Intonations of Greyed-Purple Group 185A. Shape: Urn-shaped. Texture: Glabrous. Size: 7 to 10 mm (h)×11 to 12 mm (w).

*Pedicel*.—Surface: With fine hairs and stipitate glands. Length: Variable. 70 to 115 mm in length. Diameter: 4 mm average diameter. Color: Yellow-Green Group 144A. Intonations of Greyed-Purple Group 185B. Strength: Strong. Texture: Pappilate. Borne: Multiple flower buds per stem, generally 5 to 8. Flowers held upright.

*Peduncle*.—Surface: Leathery and slightly rugose. Length: Variable. 70 to 115 mm in length. Diameter: 5 to 6 mm average diameter. Color: Yellow-Green Group 144B. Intonations of Greyed-Purple Group 184B. Strength: Strong. Borne: Multiple flower buds per stem, generally 5 to 8.

THE PLANT

*Growth*.—Vigorous.

*Plant habit*.—Upright. When grown as a field plant, the average plant height is 120 cm and the average plant width is 90 cm.

*Stems*.—Stem color: Young wood: Yellow-Green Group 144A. Older wood: Yellow-Green Group 144B. Intonations: Greyed-Purple Group 184B on new shoots and on older stems. Stem surface texture: Young wood: Smooth. Older wood: Smooth.

*Prickles*.—Present. Incidence: Average of 7 per each 10 cm of stem. Size: Average length: 6 mm. Color: Immature prickles: Yellow-Green Group 144C. Mature prickles: Yellow-Green Group 144C. Senescing to Greyed-Brown Group N199B. Shape: Concave to deeply concave. Anthocyanin: Color: Greyed-Purple Group 184B, most commonly on mature prickles.

*Leaves*.—Normally 7 leaflets on normal leaves in middle of the stem. Venation pattern: Pyramidal net pattern. Leaf size: 180 to 235 mm (l)×130 to 170 mm (w). Abundance: Average.

*Leaflets*.—Size: Average size of the terminal leaflet is 75 mm (l)×55 mm (w). Shape: Obtuse. Base: Obtuse. Apex: Cuspidate. Margins: Serrated. Surface: Semi-glossy. Texture: Upper side of leaflet: Smooth. Under side of leaflet: Leathery.

*Color, mature foliage*.—Upper Leaflet Surface: Yellow-Green Group 147A and Green Group 137B. Lower Leaflet Surface: Yellow-Green Group 147B.

*Color, juvenile foliage*.—Upper Leaflet Surface: Yellow-Green Group N144B. Lower Leaflet Surface: Yellow-Green Group N144D.

*Anthocyanin intonation*.—Greyed-Purple Group 183B. Location: Most commonly on juvenile foliage, and midrib and margins of mature leaflets.

*Arrangement*.—Odd pinnate.

*Venation*.—Reticulate.

*Stipules*.—Size: 25 to 25 mm (l)×6 to 12 mm (w). Stipule color: Yellow-Green Group 144A and Green Group 137A. Anthocyanin: Greyed-Purple Group 184B, present on mid-rib and veins. Stipitate glands: Abundant on margins. Margins: Cilliate. Texture: Leathery. Shape: Apex: Apiculate. Base: Flat.

*Petiole*.—Length: Average 50 mm. Diameter: Average 2 mm. Petiole color: Yellow-Green Group 146A, 146B and 146C. Underneath: Yellow-Green Group 144B and 144C. Margins: With fine hairs and limited numbers of stipitate glands. Anthocyanin: Greyed-Purple Group 184B, present on mid-rib. Prickles: A few small prickles underneath. Stipitate Glands: Limited numbers of stiptiate glands. Texture: Pubescent.

*Petiole rachis*.—Length: Average 65 to 70 mm. Diameter: Average 2 mm. Color: Yellow-Green Group 144B and 144C. Anthocyanin present on upper side: Greyed-Purple Group 184B. Margins: Few stipitate glands present. Prickles: A few small prickles underneath. Stipitate glands: Limited numbers of stipitate glands on margins.

Hips/seed formation: None observed.

Winter hardiness: To date, the variety has been grown successfully in Zones 5 to 8.

Disease resistance: Very good resistance to Powdery mildew (*Sphaerotheca pannosa*) and blackspot (*Diplocarpon rosae*) diseases under normal growing conditions in Jackson County, Oreg.

I claim:

1. A new and distinct variety of rose plant, as described and illustrated herein.

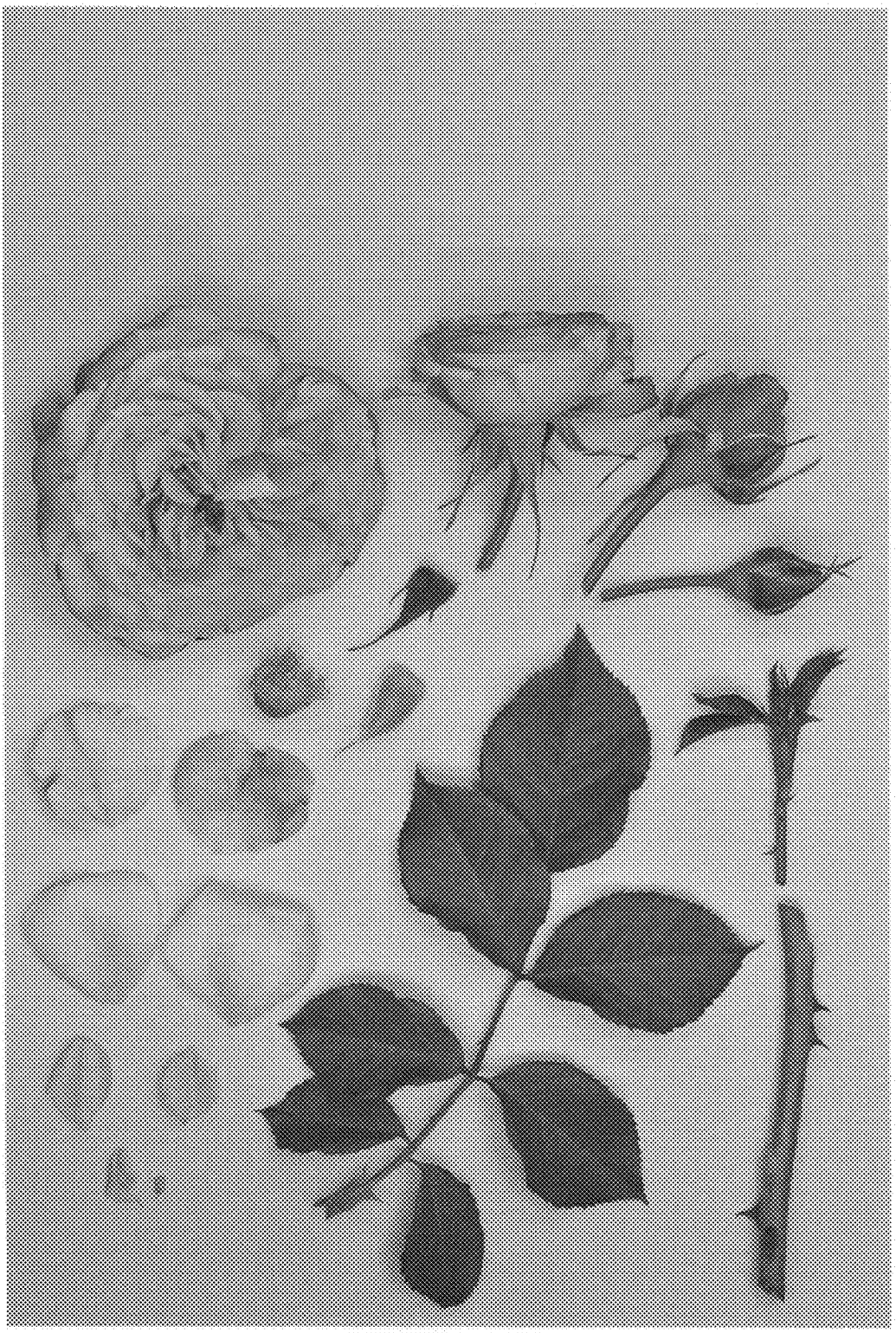

* * * * *